US012765822B2

(12) United States Patent
Lim et al.

(10) Patent No.: US 12,765,822 B2
(45) Date of Patent: Oct. 20, 2026

(54) DEVICES, SYSTEMS, AND METHODS FOR OBJECT DEPTH ESTIMATION

(71) Applicant: Boston Scientific Scimed, Inc., Maple Grove, MN (US)

(72) Inventors: Kian S. Lim, Shrewsbury, MA (US); Longquan Chen, Lexington, MA (US); Niraj Prasad Rauniyar, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 147 days.

(21) Appl. No.: 18/897,365

(22) Filed: Sep. 26, 2024

(65) Prior Publication Data

US 2025/0107735 A1 Apr. 3, 2025

Related U.S. Application Data

(60) Provisional application No. 63/586,441, filed on Sep. 29, 2023.

(51) Int. Cl.
*A61B 5/00* (2006.01)
*A61B 5/20* (2006.01)

(52) U.S. Cl.
CPC ............ *A61B 5/201* (2013.01); *A61B 5/0084* (2013.01)

(58) Field of Classification Search
CPC ..................................................... A61B 90/06
See application file for complete search history.

(56) References Cited

U.S. PATENT DOCUMENTS

2015/0366571 A1 12/2015 Navve et al.
2018/0192982 A1 7/2018 Pereira et al.
2023/0092920 A1 3/2023 Lim et al.
2023/0115488 A1 4/2023 Shelton et al.
2023/0390019 A1 12/2023 Lim et al.

FOREIGN PATENT DOCUMENTS

WO 2023239633 A1 12/2023

*Primary Examiner* — Joseph M Santos Rodriguez
(74) *Attorney, Agent, or Firm* — Seager, Tufte & Wickhem, LLP

(57) ABSTRACT

Medical systems and related methods useful to estimate the depth of a target are described. The system may include a medical device that includes a handle and a shaft, the medical device also including an imager, a processor, and at least one laser source coupled to a first laser fiber and a second laser fiber. The first and second laser fibers may be configured to transmit respective first and second collimated beams of light onto a target simultaneously without fragmenting the target. The processor may be configured to determine a depth of the target from a proximal facing surface of the target to a distal facing surface of the target based on pixel characteristics of the first and second collimated beams of light in at least one image generated by the imager.

20 Claims, 4 Drawing Sheets

1/8" SPHERE AT 10mm AWAY FROM CAMERA
(IN SALINE SOLUTION)

1/8" SPHERE AT 10mm AWAY FROM CAMERA
(IN SALINE SOLUTION)

DEVICES, SYSTEMS, AND METHODS FOR OBJECT DEPTH ESTIMATION

CROSS-REFERENCE TO RELATED APPLICATIONS

This application claims the benefit of priority to U.S. Provisional Application No. 63/586,441, filed on Sep. 29, 2023, which is incorporated by reference herein in its entirety.

TECHNICAL FIELD

Aspects of the present disclosure generally relate to medical devices, system, and procedures related thereto. In particular, some aspects relate to medical systems, devices, and methods for object depth estimation within the body of a patient.

BACKGROUND

The manner in which urinary or kidney stones may be removed from patients may depend on the size of the stones. For example, some smaller stones, or fragments of stones, may be of an adequate size to pass through a bodily lumen, e.g., the urinary tract, and out of the body. However, some larger stones, or residual fragments of stones, may require removal via an endoscopic procedure, such as retrieval by a retrieval device, e.g., a nitinol basket, grasper, etc., or further fragmentation into smaller pieces via lithotripsy. Any residual fragments greater than 5 mm may further require follow-up re-intervention to remove such fragments from a patient. Thus, accurate stone size estimation or measurement of the length, width, and depth of a stone may be an important aspect of stone removal and lithotripsy.

However, obtaining accurate measurements and estimations of stone size and dimensions is a known problem with existing devices. The current disclosure may solve one or more of these issues or other issues in the art.

SUMMARY

The present disclosure includes medical devices and related methods useful for analyzing targets within the body, including kidney stones. For example, the present disclosure includes a medical system comprising a medical device including a handle and a shaft defining a working channel having a distal opening at a distal end of the shaft, the distal end also including an imager, a processor, and at least one laser source coupled to a first laser fiber and a second laser fiber, wherein each of the first laser fiber and the second laser fiber extends through the shaft. The first and second laser fibers may be configured to transmit respective first and second collimated beams of light onto a target simultaneously without fragmenting the target, and the processor may be configured to determine a depth of the target from a proximal facing surface of the target to a distal facing surface of the target based on pixel characteristics of the first and second collimated beams of light in at least one image generated by the imager. Optionally, the handle of the medical device may include the processor.

According to some aspects, the processor is configured to determine the pixel characteristics of the first and second collimated beams of light by comparing a first image in which the first and second collimated beams of light are directed on the target to a second image in which the first and second collimated beams of light are directed on a reference surface adjacent to the target. The processor may store data including a series of possible pixel distances between the first and second collimated beams of light, and each one of the series of possible pixel distances may correlate to a possible distance between the proximal facing surface of the target and the imager or between the reference surface and the imager. The processor may be configured to identify a pixel distance between the first and second collimated beams of light in each of the first image and the second image, and calculate the depth of the target based on the pixel distances. In some examples, the processor may be configured to identify and record the pixel distances automatically. Additionally or alternatively, the processor may be configured to identify and record the pixel distances when prompted by a user. According to some aspects, the medical system further comprises a display configured to show the at least one image, wherein the processor may be configured to transmit the determined depth of the target to the display with the at least one image. In some examples, a wavelength of the first collimated beam of light is blue or green, and a wavelength of the second collimated beam of light is the same or different than the wavelength of the first collimated beam of light. For example, the wavelength of the first collimated beam of light may be different than the wavelength of the second collimated beam of light.

The present disclosure also includes a method of analyzing a target in a body of a subject, the method comprising introducing a medical device into a lumen or an organ of the body that includes the target, and positioning a distal end of the medical device proximate the target, wherein the distal end includes a first laser fiber, a second laser fiber, and an imager. The method may further comprise generating, via the imager, a first image of the target while the first laser fiber transmits a first collimated beam of light onto the target and the second laser fiber transmits a second collimated beam onto the target, generating, via the imager, a second image of the target while the first laser fiber transmits the first collimated beam of light on a reference surface adjacent to the target and the second laser fiber transmits the second collimated beam onto the reference surface, and calculating, via a processor, a depth of the target based on pixel characteristics of the first and second collimated beams of light in the first and second images. According to some aspects, the processor may store data including a series of possible pixel distances between the first and second collimated beams of light, and each one of the series of possible pixel distances may correlate to a possible distance between the target and the imager and/or between the reference surface and the imager. Calculating the depth of the target may include comparing the pixel characteristics of the first and second collimated beams of light to the stored data. The target may be a kidney stone, for example. In one or more aspects, a wavelength of each of the first collimated beam of light and the second collimated light may be blue or green, and the wavelength of the second collimated beam of light may be the same or different than the wavelength of the first collimated beam of light. In some aspects, the calculating the depth of the target may include the processor automatically identifying a pixel distance between the first and second collimated beams of light in each of the first image and the second image. In some examples, the calculating the depth of the target may include the processor identifying a pixel distance between the first and second collimated beams of light in each of the first image and the second image in response to user input.

The present disclosure also includes a method of analyzing a target in a body of a subject, the method comprising positioning a distal end of a medical device proximate the target, wherein the distal end includes a first laser fiber, a second laser fiber, and an imager; generating, via the imager, a first image of the target while the first laser fiber transmits a first collimated beam of light on the target and the second laser fiber transmits a second collimated beam onto the target; generating, via the imager, a second image of the target while the first laser fiber transmits the first collimated beam of light on a reference surface adjacent to the target and the second laser fiber transmits the second collimated beam onto the reference surface; identifying, via a processor, a pixel distance between the first and second collimated beams of light in each of the first image and the second image; and calculating, via the processor, a depth of the target based on the pixel distances. The processor may store data including a series of possible pixel distances between the first and second collimated beams of light, and each one of the series of possible pixel distances may correlate to a possible distance between the target and the imager or between the reference surface and the imager. The method may further comprise showing the calculated depth of the target on a display.

BRIEF DESCRIPTION OF THE FIGURES

The accompanying drawings, which are incorporated in and constitute a part of this application, illustrate exemplary aspects that, together with the written descriptions, serve to explain the principles of this disclosure. Each figure depicts one or more exemplary aspects according to this disclosure, as follows.

DETAILED DESCRIPTION

Figure 1A:
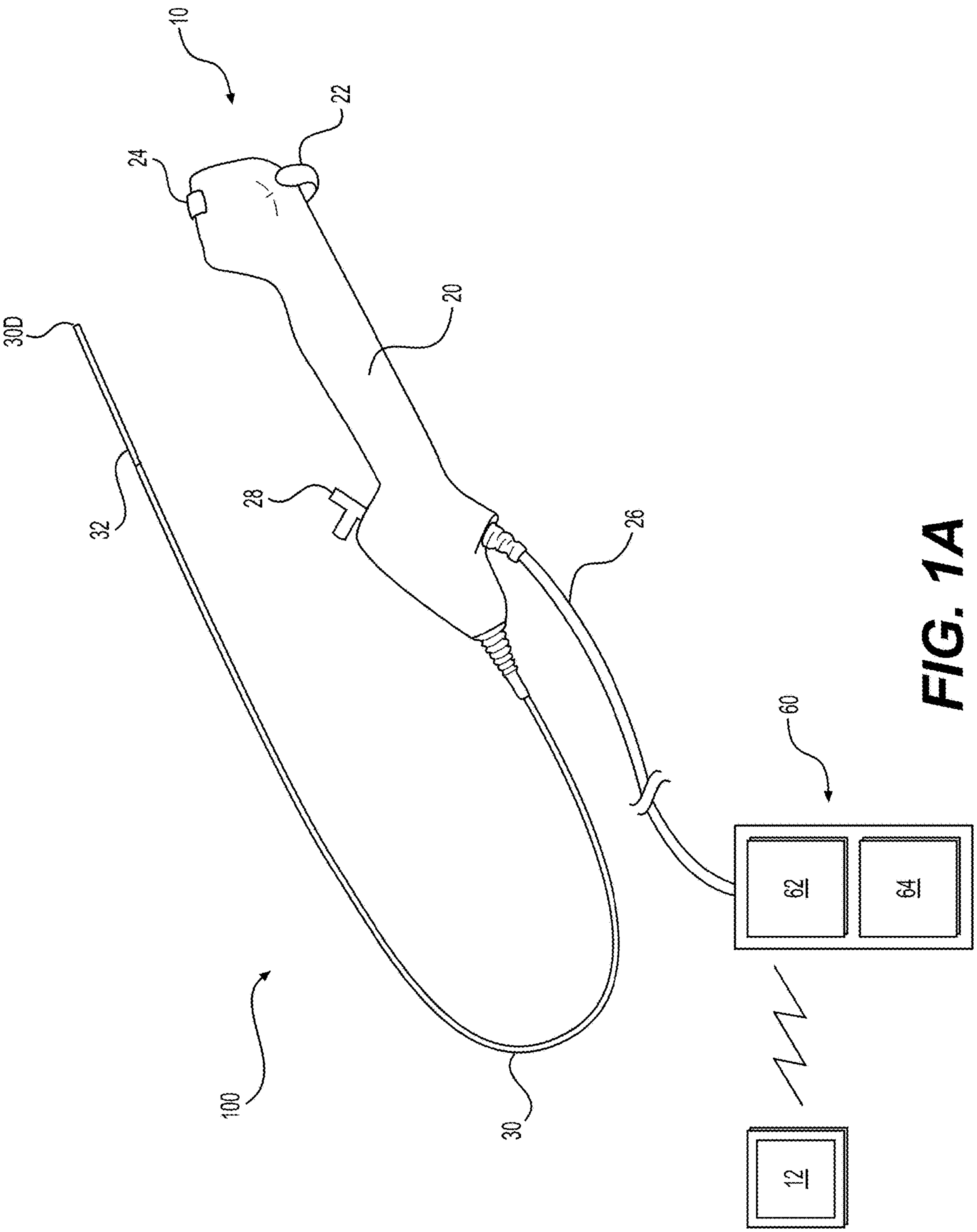
FIG. 1A depicts an exemplary scope.

Reference will now be made in detail to examples of the present disclosure described above and illustrated in the accompanying drawings. Wherever possible, the same reference numbers will be used throughout the drawings to refer to the same or like parts.

In some techniques, where an imaging device is used to visualize a stone, a surgeon may manually estimate stone size by comparing an unknown dimension of the stone (e.g., a perceived maximum width) with a known dimension of a medical scope or accessory instrument, e.g., a diameter of an opening of a retrieval device. These estimations are often inaccurate, owing to the inherent challenges associated with measuring a three-dimensional object from a two-dimensional image, especially when the image is of low resolution or visibility. Because of these inaccuracies, the surgeon may be required to remove and/or further fragment more stones than medically required, increasing operation times. Even more time may be lost if the surgeon introduces a retrieval device based on the estimated stone size, then finds the fragment too big for the device, requiring removal of the retrieval device and/or further fragmentation of the stone.

The width, length, and depth of a stone may be all important dimensions for stone size estimation. The width and length of the stone may be seen by a camera positioned at a distal tip of a medical device and estimated or measured by comparing known dimensions and values. However, the depth of a stone may be more difficult to estimate or measure as the depth may not be in fully view of the camera. The depth of the stone may be defined as the dimension between a proximal face of the stone to the distal face of the stone or as the dimension between a proximal face of the stone and a reference surface, such as an internal surface of a kidney. For example, for stone removal, the depth of the stone may be an important parameter when determining which tool or size of medical tool should be used. The disclosed methods and devices may produce more accurate measurements and estimations of stones than existing methods and devices.

Aspects of the disclosure are now described with reference to exemplary systems and methods for measuring and estimating stone size. Some aspects are described with reference to medical procedures where a scope is guided through a body until a distal end of the scope is located in a body cavity including one or more stone objects. For example, the scope may include an elongated sheath that is guided through a urethra, a bladder, and a ureter until a distal end of the sheath is located in a calyx of a kidney, adjacent one or more kidney stones. References to a particular type of procedure, such as medical; body cavity, such as a calyx; and stone object, such as a kidney stone, are provided for convenience and not intended to limit the disclosure unless claimed. Accordingly, the concepts described herein may be utilized for any analogous device or method—medical or otherwise, kidney-specific or not.

Both the foregoing general description and the following detailed description are exemplary and explanatory only and are not restrictive of the features, as claimed. As used herein, the terms “comprises,” “comprising,” “having,” “including,” or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, “about,” “substantially,” “generally,” and “approximately” are used to indicate a possible variation of ±10% in a stated value or characteristic.

An exemplary system 100 is now described with reference to FIG. 1A. System 100 comprises a medical device 10, e.g., a scope, which may be in connection with equipment 60 supporting the medical device 10. For example, medical device 10 may include a bronchoscope, duodenoscope, endoscope, colonoscope, ureteroscope, etc., and/or may include a catheter, tool, instrument, or the like, having a shaft/catheter that extends distally from a handle. In this example, medical device 10 includes a handle 20 with at least one actuator, e.g., first actuator 22 and second actuator 24 a port 28, and a shaft 30 with a steerable portion 32 and distal end 30D.

Actuators 22, 24 may receive user input and transmit the user input to shaft 30. Each actuator 22, 24 may include a lever, knob, slider, joystick, button, or other suitable mechanism. For example, first actuator 22 may include a lever configured to articulate steerable portion 32, e.g., via pull wires within shaft 30, and second actuator 24 may include a button configured to actuate and/or control other aspects of medical device 10, e.g., turning on/off laser sources and/or capturing images.

Equipment 60 may be configured to supply medical device 10 with vacuum/suction, fluid (e.g., liquid, air), and/or power via umbilicus 26. As shown in FIG. 1A, equipment 60 may include a processing unit 62, e.g., operable with medical device 10. For example, processing unit 62 may help generate a visual representation of image data and/or transmit the visual representation to one or more interface devices, e.g., a display 12. According to some aspects, processing unit 62 may augment the visual representation. Display 12 may include, e.g., a touch-screen display, capable of displaying images captured using medical device 10 and processing unit 62.

Equipment 60 may also include at least one laser source 64. For example, laser source 64 may include one or more laser pointer(s), gas laser source(s), liquid laser source(s), semiconductor laser source(s), excimer laser source(s), or laser diode(s), etc., and/or any suitable non-laser device, e.g., a LED with a collimator.

While FIG. 1A shows processing unit 62 and laser source 64 coupled to medical device 10 by umbilicus 26, in other examples, one or both of processing unit 62 and/or laser source 64 may be incorporated into medical device 10. For example, processing unit 62 and/or laser source 64 may be included in handle 20. In some examples, one laser source 64 may be capable of generating a plurality of two more different wavelengths or beams. In other examples, each laser source 64 may only be capable of generating one wavelength, e.g., medical device 10 or equipment 60 including multiple laser sources 64. The intensity, wavelength(s), and other aspects of the light generated by laser source(s) may be configured to avoid altering, e.g., fragmenting, an anatomical object such as a kidney stone. In some examples, one or more laser sources 64 may generate a first wavelength of light and a second wavelength of light different from the first wavelength of light, e.g., red, green, or blue. In at least one example, a first laser source 64 is configured to generate green light and a second laser source 64 is configured to generate blue light. This example may be advantageous in circumstances where the target or a reference surface being imaging by system 100 is red in color. For example, a reference surface may be brownish-red in color in the case of an interior surface of a kidney. Laser source(s) 64 may generate collimated beams.

As mentioned above, umbilicus 26 may operably couple medical device 10 and equipment 60. Umbilicus 26 may sheath various cables and wirings for electric/electronic connection and/or one or more laser fibers. For example, in the case of two laser sources 64, umbilicus 26 may sheath a first laser fiber 43 and a second laser fiber 45 (see FIGS. 1B and 1C). Laser fibers 43, 45 may be Holmium fibers, or other types of laser fibers or optical fibers with collimator. Each of first laser fiber 43 and second laser fiber 45 may be removably couplable to corresponding laser source(s) 64 via, for example, a laser-to-laser coupler. The coupler may include a soldering or intermediary lenses which may assist with the coupling between fibers 43, 45 and laser source(s) 64. Any suitable number of laser fibers may be utilized, e.g., three, four, or five or more laser fibers.

Referring again to FIG. 1A, port 28 may be on a distal portion of handle 20 and include one or more openings in communication with a working channel 34 of shaft 30. A suitable accessory instrument or tool, e.g., lithotripsy device, grasper, retrieval device, etc., may be inserted through port 28 and moved distally through shaft via working channel 34.

Shaft 30 may further include one or more lumen(s) for receiving pull wires and/or other wiring, cables, and/or laser fibers such as laser fibers 43, 45. For example, laser fibers 43, 45 may extend through lumen(s) of shaft 30 offset from the central axis or through a central opening defined by an outer sheath of shaft 30. Each of first laser fiber 43 and second laser fiber 45 may include a single, continuous, monolithic piece of fiber. In alternatives, one or both of first laser fiber 43 or second laser fiber 45 may include multiple pieces that are in optical communication with one another (e.g., joined by connected or fused together).

Figure 1B:
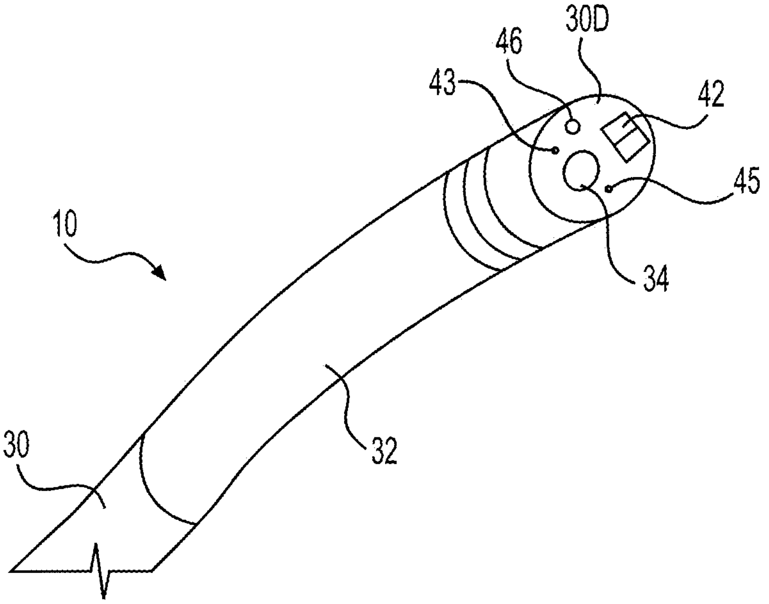
FIG. 1B depicts an exemplary distal end of the scope of FIG. 1A.
Figure 1C:
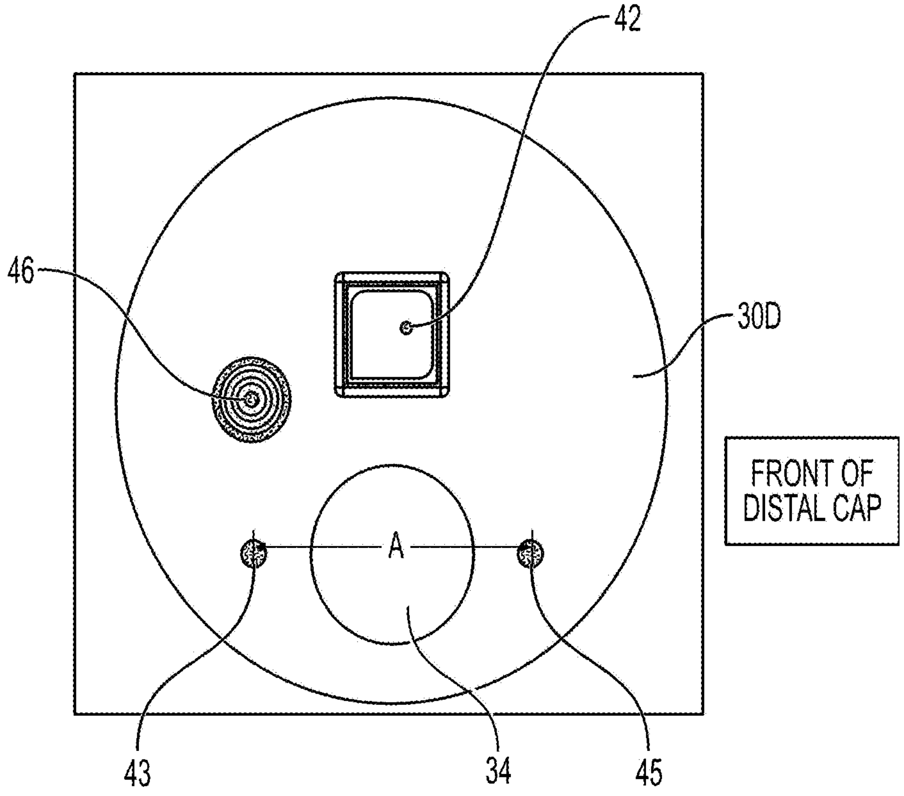
FIG. 1C depicts an exemplary distal face of the scope of FIG. 1B.

As shown in FIGS. 1B and 1C, distal end 30D of shaft 30 may include a distal opening of working channel 34, imager 42 (e.g., camera or other imaging device), a light source 46 (e.g., light-emitting diode LED), and distal ends of laser fibers 43, 45. In some examples, shaft 30 may include a cap covering portions of distal end 30D, e.g., protecting features such as imager 42, light source 46, and laser fibers 43, 45. In some examples, imager 42 may include a camera comprising a CMOS sensor. In some examples, imager 42 may include fiber optics in communication with a sensor or other device within shaft 30 or handle 20. In some examples, light source 46 may include a plastic optical fiber ("POF") device or a light-emitting diode (LED).

As shown in FIGS. 1B and 1C, first laser fiber 43 and second laser fiber 45 may be configured to transmit light from distal end 30D of shaft 30. As discussed above, while two laser fibers are depicted in FIGS. 1A-1C, system 100 may further include additional laser fibers, e.g., a third laser fiber, a fourth laser fiber, etc. Laser fibers 43 and 45 may be in communication with laser source(s) 64 of equipment 60 (or disposed within handle 20). Each laser source(s) 64 may transmit or project a collimated beam of light, which may travel through corresponding laser fibers 43, 45. As shown in the example depicted in FIG. 1C, laser fibers 43 and 45 may be on diametrically opposite sides of the distal opening of working channel 34, e.g., each adjacent to the distal opening. Other configurations are contemplated herein (e.g., both laser fibers being on the same side of shaft 30 and the same side of distal end 30D, three laser fibers disposed symmetrically in a triangular configuration about the distal opening, etc.)

The distance A between a center of first laser fiber 43 and a center of second laser fiber 45 may be consistent regardless of the distance light is transmitted. For example, the distance between first laser fiber 43 and second laser fiber 45 at distal end 30D may range from about 1 mm to about 7 mm, e.g., 1 mm, 2 mm, 3 mm, 4 mm, 5 mm, 6 mm, or 7 mm, etc.

Figure 2A:
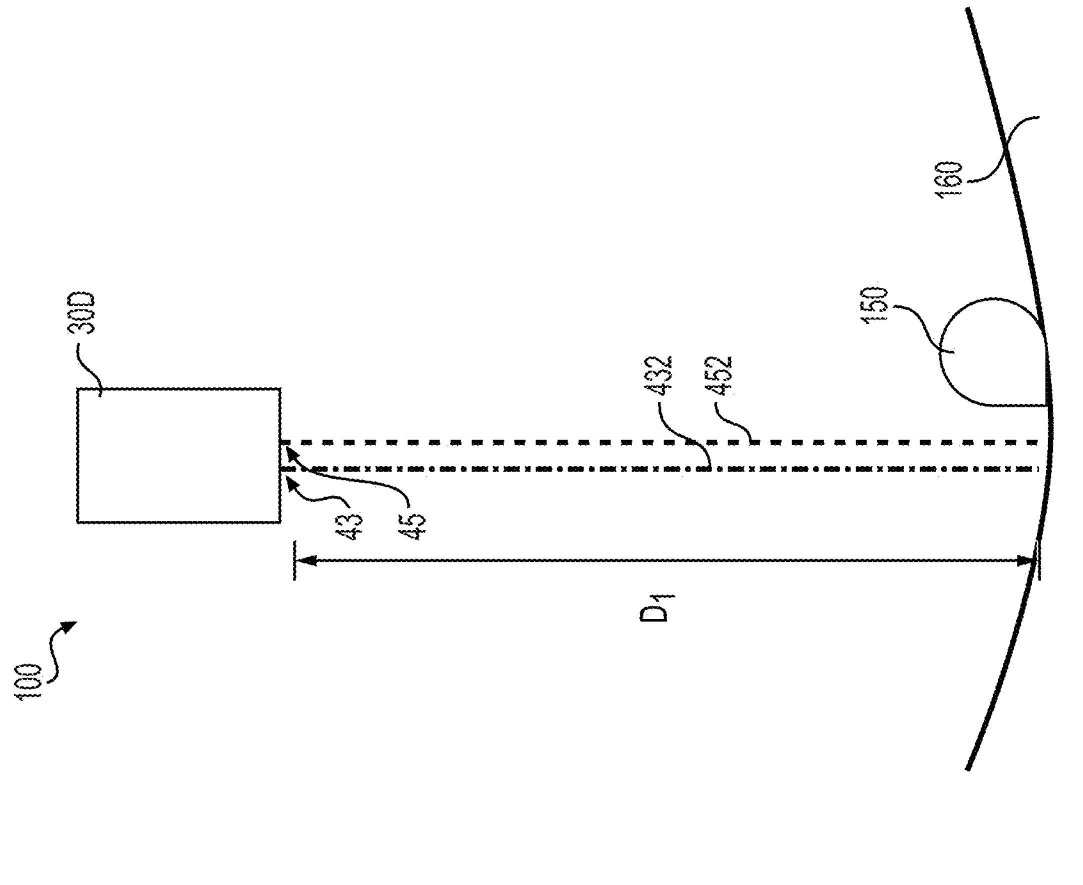
FIG. 2A depicts an exemplary distal end of the scope of FIG. 1A with lasers pointed at a reference surface.
Figure 2B:
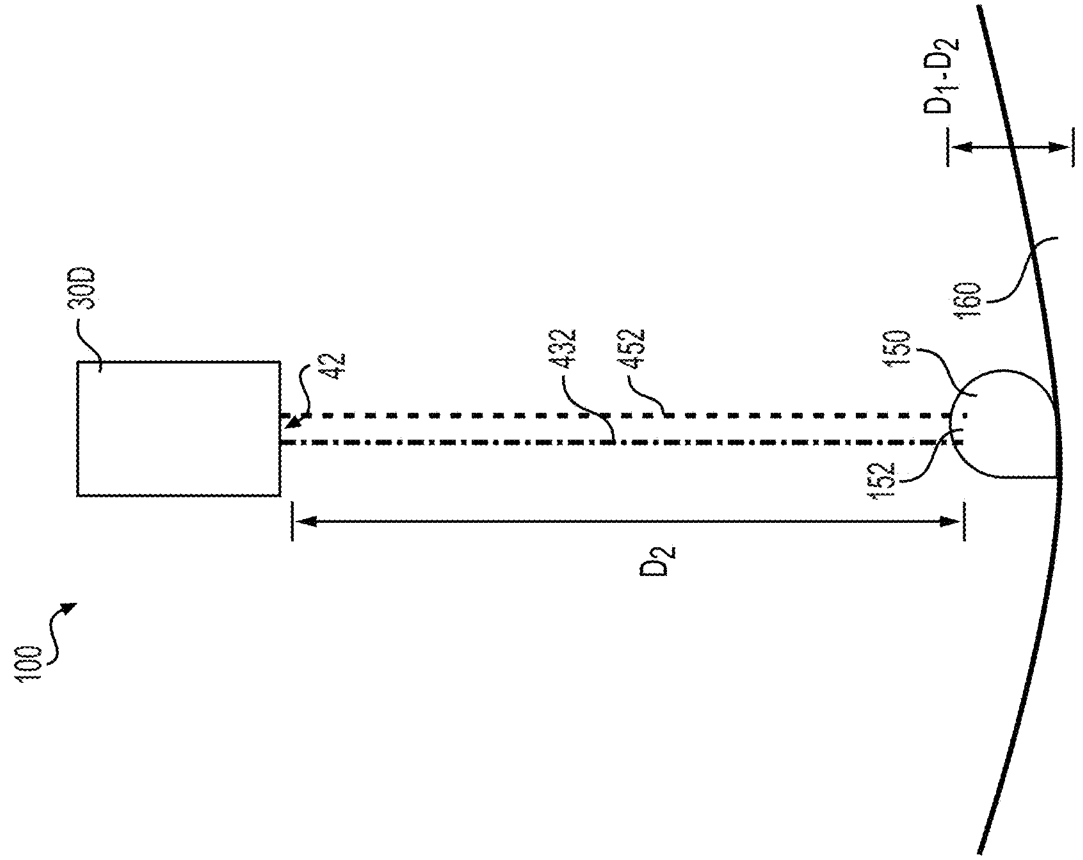
FIG. 2B depicts an exemplary distal end of the scope of FIG. 1A with lasers pointed at a target.

As shown in FIGS. 2A and 2B, laser fibers 43, 45 may transmit parallel, collimated beams, e.g., a first collimated beam 432 (e.g., a first collimated beam of light) and a second collimated beam 452 (e.g., a second collimated beam of light), respectively. The distance A between the center of first laser fiber 43 and the center of second laser fiber 45 may be used to calculate, e.g., to estimate using known parameters, a depth of a target 150 within a body lumen or organ. By moving the imaging device in and away from the target, the pixel count between the two beams 432, 452 may change accordingly. Knowing the fixed distance A between laser fibers 43, 45 permits calculation of an estimated distance between the imager and the target and/or the imager and a reference surface by changes in pixel count. For example, calibrating the medical device in a controlled environment may provide a relationship between pixel count and distance between the imager and the target and/or the imager and a reference surface. For example, the depth may be calculated from the distance D1 between the distal end 30D of medical device 10 (e.g., imager 42) to a reference surface 160 proximate the target and the distance D2 between the distal end 30D/imager 42 to target 150 (e.g., proximal facing surface 152 of target 150).

Figure 3A:
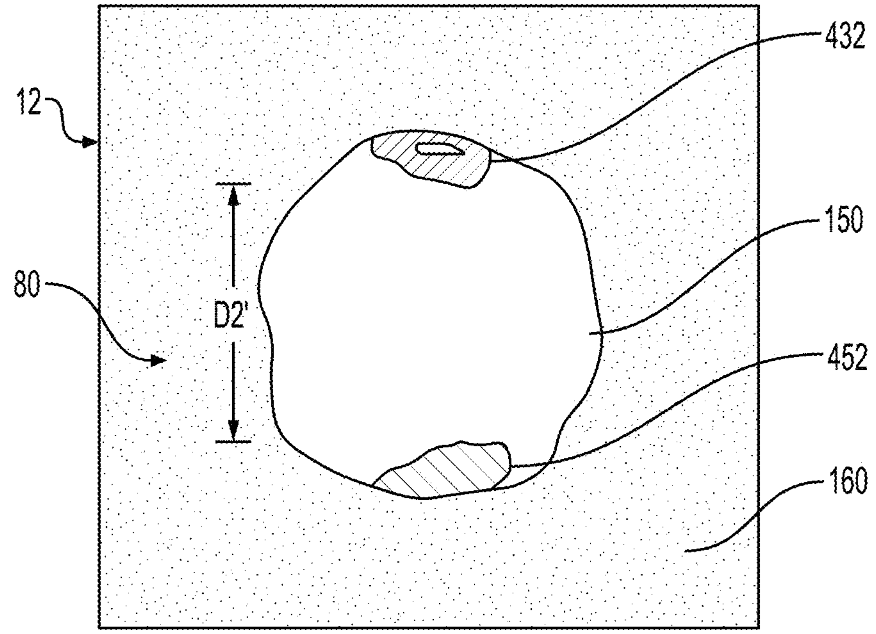
FIG. 3A-3B depict exemplary images obtain from the scope of FIG. 1A.

FIG. 3A illustrates an exemplary image 80 generated or captured via imager 42, which may be shown on a display 12. In generating image 80, distal end 30D (and thus imager 42) of medical device 10 is proximate target 150. For example, distal end 30D may be positioned adjacent to, e.g., approximately 10 mm away from, target 150. While target 150 may be various anatomical features, in this example, target 150 is depicted as a kidney stone, e.g., having a spherical shape with a diameter of about ⅛ inch. The first collimated beam of light 432 is transmitted onto target 150 via first laser fiber 43 and the second collimated beam of light 452 is transmitted onto target 150 via second laser fiber 45. The center of first collimated beam of light 432 and the center of second collimated beam of light 452 are separated by distance A, e.g., 3 mm, approximately equal to the distance between first laser fiber 43 and second laser fiber 45 on distal end 30D. A processor of medical system 100 may be configured to calculate the depth of target 150, e.g., based on known parameters and calibration of system 100. For example, processing unit 62 of equipment 60, a processor within handle 20 of medical device 10, or another processing aspect of system 100 may estimate the depth (e.g., the difference between D1 and D2) of target 150. A user may subsequently assess the depth of target 150 and other dimensions (e.g., length and width) to a preset size threshold or thresholds to determine, for example, whether target 150 may be removed via medical device 10 (e.g., via working channel 34). Otherwise, the user may determine that fragmentation into smaller pieces (e.g., via lithotripsy) would be appropriate prior to removal.

Referring again to FIGS. 2A and 2B, the depth of target 150 may be calculated from first determining distance D1 between distal end 30D/imager 42 and reference surface 160 and distance D2 between distal end 30D/imager 42 and target 150 (e.g., proximal facing surface 152 of target 150). As mentioned above, while target 150 in this example is a kidney stone, it should be understood that neither reference surface 160 nor target 150 are intended to be limited to kidneys or kidney stones. D1 and D2 may be determined by analyzing images wherein first and second collimated beams 432, 452 are directed to target 150 (FIG. 3A) and wherein first and second collimated beams 432, 452 are directed to reference surface 160 proximate target 150, e.g., a surface adjacent to target 150 (e.g., adjacent to a distal facing surface of target 150).

Figure 3B:
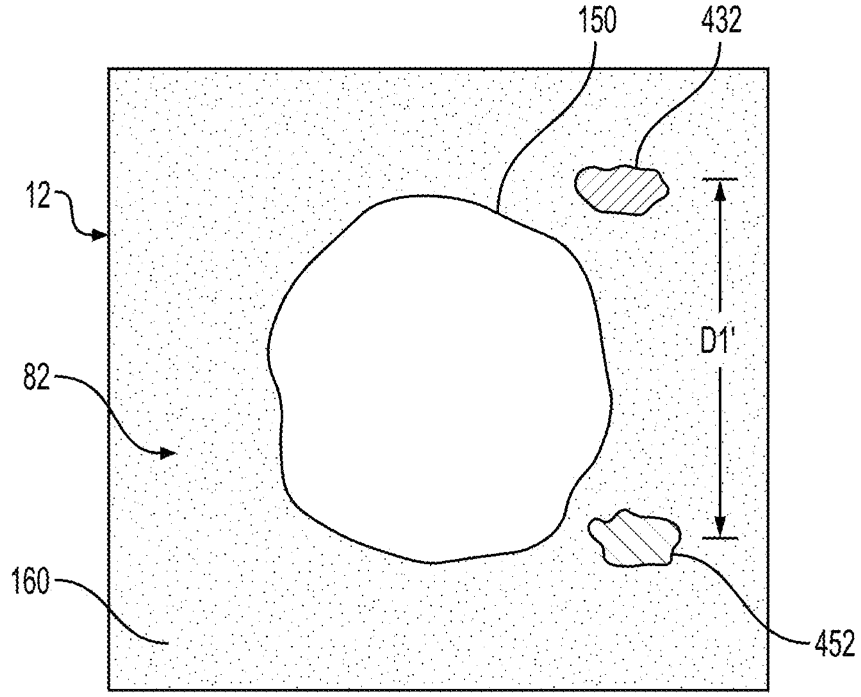

Pixel characteristics of the first and second collimated beams 432, 452 in images of target 150 may be used to determine the depth of target 150. As seen in FIG. 3A, for example, a pixel distance D2' between first collimated beam 432 and second collimated beam 452 may be determined in image 80, generated by imager 42, where both first collimated beam 432 and second collimated beam 452 are transmitted onto target 150. Similarly, in FIG. 3B, the pixel distance D1' between first collimated beam 432 and second collimated beam 452 in image 82, generated by imager 42, where both first collimated beam 432 and second collimated beam 452 are projected onto reference surface 160. A processor of medical system 100 may be configured to determine the depth of target 150 (e.g., from a proximal facing surface to a distal facing surface of target 150) based on pixel characteristics of the beams of light 432, 452 in the images 80, 82. The difference between distance D1' and distance D2' may provide an estimate of the depth of target 150. For example, the pixel distances may be calibrated to data correlating pixel distance and distances between imager 42 and an object appearing in the image. The relationship between pixel distances and the distance between imager 42 and target 150 may be calibrated in a controlled environment, e.g., knowing fixed distance A. Such calibration data may be stored within the processor. Thus, for example, a table of the data may include a series of pixel distances, each pixel distance correlating to a particular distance of an imaged object from imager 42. The table of the data may be created during calibration. For example, based on calibrated measurements, 1 pixel may correspond to 20 mm, 2 pixels may correspond to 10 mm, 3 pixels may correspond to 6 mm, 5 pixels may correspond to 4 mm, 10 pixels may correspond to 3 mm, 20 pixels may correspond to 2 mm, 100 pixels may correspond to 0.5 mm, etc. Thus, pixel distances D1' and D2' between first collimated beam 432 and second collimated beam 452 may be used to estimate the distances D1 and D2 (FIGS. 2A and 2B), via the aforementioned pixel distance calibration. Thus, the depth of target 150 may be calculated according to the difference between D1 and D2. The processor may be configured to identify and/or record pixel distance automatically. Additionally or alternatively, the processor may be configured to identify and/or record pixel distance when prompted by a user.

In an exemplary medical procedure utilizing system 100, medical device 10 may be introduced into a lumen or an organ of a subject's body so that distal end 30D is proximate target 150 (e.g., and proximate reference surface 160). As medical device 10 is advanced through the body in the direction of target 150 and reference surface 160, a processor of system 100 (e.g., within processing unit 62 or within handle 20) and imager 42 may constantly, periodically (e.g., at pre-determined intervals), or upon meeting pre-determined conditions, generate image(s) of target 150 and/or reference surface 160. First collimated beam 432 and second collimated beam 452 may be transmitted onto target 150 or reference surface 160 in each image, e.g., one or more times, as medical device 10 is advanced.

The processor of processing unit 62 or handle 20 may be configured to identify the pixel distance between first collimated beam 432 and second collimated beam 452, e.g., automatically and/or in reply to user input as mentioned above. For example, the processor may be configured to identify the pixel distance(s) whenever first and second collimated beams 432, 452 both transition from transmitting onto target 150 from reference surface 160 or vice versa. In some examples, the processor may be configured to identify the pixel distance(s) at pre-determined time intervals. In some examples, a user may identify target 150 and reference surface 160 and enter that data to system 100 to prompt the processor to identify and/or record the pixel distances, and subsequently calculate distances D1 and D2 that correlate to the pixel distances based on data stored in the processor. The processor may be configured to calculate the depth of target 150 by subtracting D2 from D1. When calculating the depth of target 150, the processor may use a recent recorded distance D1 and/or D2, or may use a pre-determined value for D1 and/or D2. The processor may record the determined (e.g., estimated) depth of target 150. Optionally, the processor may be configured to record (e.g., store) each distance D1 and D2. The processor may be configured to transmit the distances D1, D2 and/or the determined depth of target 150 to a display 12.

While principles of the disclosure are described herein with reference to illustrative aspects for particular medical uses and procedures, the disclosure is not limited thereto. Those having ordinary skill in the art and access to the teachings provided herein will recognize additional modifications, applications, aspects, and substitution of equivalents all fall in the scope of the aspects described herein. Accordingly, the disclosure is not to be considered as limited by the foregoing description.

What is claimed is:

1. A medical system comprising:

a medical device including a handle and a shaft defining a working channel having a distal opening at a distal end of the shaft, the distal end also including an imager;

a processor; and at least one laser source coupled to a first laser fiber and a second laser fiber;

wherein each of the first laser fiber and the second laser fiber extends through the shaft, the first and second laser fibers being configured to transmit respective first and second collimated beams of light onto a target simultaneously without fragmenting the target; and wherein the processor is configured to determine a depth of the target from a proximal facing surface of the target to a distal facing surface of the target based on pixel characteristics of the first and second collimated beams of light in at least one image generated by the imager.

2. The medical system of claim 1, wherein the handle of the medical device includes the processor.

3. The medical system of claim 1, wherein the processor is configured to determine the pixel characteristics of the first and second collimated beams of light by comparing a first image in which the first and second collimated beams of light are directed on the target to a second image in which the first and second collimated beams of light are directed on a reference surface adjacent to the target.

4. The medical system of claim 3, wherein the processor stores data including a series of possible pixel distances between the first and second collimated beams of light, and each one of the series of possible pixel distances correlates to a possible distance between the proximal facing surface of the target and the imager or between the reference surface and the imager.

5. The medical system of claim 4, wherein the processor is configured to identify a pixel distance between the first and second collimated beams of light in each of the first image and the second image, and calculate the depth of the target based on the pixel distances.

6. The medical system of claim 5, wherein the processor is configured to identify and record the pixel distances automatically.

7. The medical system of claim 5, wherein the processor is configured to identify and record the pixel distances when prompted by a user.

8. The medical system of claim 1, further comprising a display configured to show the at least one image, wherein the processor is configured to transmit the determined depth of the target to the display with the at least one image.

9. The medical system of claim 1, wherein a wavelength of the first collimated beam of light is blue or green, and a wavelength of the second collimated beam of light is the same or different than the wavelength of the first collimated beam of light.

10. The medical system of claim 9, wherein the wavelength of the first collimated beam of light is different than the wavelength of the second collimated beam of light.

11. A method of analyzing a target in a body of a subject, the method comprising:

introducing a medical device into a lumen or an organ of the body that includes the target;

positioning a distal end of the medical device proximate the target, wherein the distal end includes a first laser fiber, a second laser fiber, and an imager;

generating, via the imager, a first image of the target while the first laser fiber transmits a first collimated beam of light onto the target and the second laser fiber transmits a second collimated beam onto the target;

generating, via the imager, a second image of the target while the first laser fiber transmits the first collimated beam of light on a reference surface adjacent to the target and the second laser fiber transmits the second collimated beam onto the reference surface; and calculating, via a processor, a depth of the target based on pixel characteristics of the first and second collimated beams of light in the first and second images.

12. The method of claim 11, wherein the processor stores data including a series of possible pixel distances between the first and second collimated beams of light, and each one of the series of possible pixel distances correlates to a possible distance between the target and the imager or between the reference surface and the imager.

13. The method of claim 12, wherein calculating the depth of the target includes comparing the pixel characteristics of the first and second collimated beams of light to the stored data.

14. The method of claim 11, wherein the target is a kidney stone.

15. The method of claim 11, wherein a wavelength of each of the first collimated beam of light and the second collimated beam of light is blue or green, and the wavelength of the second collimated beam of light is the same or different than the wavelength of the first collimated beam of light.

16. The method of claim 11, wherein the calculating the depth of the target includes the processor automatically identifying a pixel distance between the first and second collimated beams of light in each of the first image and the second image.

17. The method of claim 11, wherein the calculating the depth of the target includes the processor identifying a pixel distance between the first and second collimated beams of light in each of the first image and the second image in response to user input.

18. A method of analyzing a target in a body of a subject, the method comprising:

positioning a distal end of a medical device proximate the target, wherein the distal end includes a first laser fiber, a second laser fiber, and an imager;

generating, via the imager, a first image of the target while the first laser fiber transmits a first collimated beam of light on the target and the second laser fiber transmits a second collimated beam onto the target;

generating, via the imager, a second image of the target while the first laser fiber transmits the first collimated beam of light on a reference surface adjacent to the target and the second laser fiber transmits the second collimated beam onto the reference surface;

identifying, via a processor, a pixel distance between the first and second collimated beams of light in each of the first image and the second image; and calculating, via the processor, a depth of the target based on the pixel distances.

19. The method of claim 18, wherein the processor stores data including a series of possible pixel distances between the first and second collimated beams of light, and each one of the series of possible pixel distances correlates to a possible distance between the target and the imager or between the reference surface and the imager.

20. The method of claim 18, further comprising showing the calculated depth of the target on a display.

* * * * *